United States Patent
Lopez Ondevilla et al.

(10) Patent No.: US 11,950,612 B2
(45) Date of Patent: Apr. 9, 2024

(54) SYSTEM FOR PROTECTING AND SECURING BAGS IN BULK HPP EQUIPMENT AND ASSOCIATED METHOD

(71) Applicant: HIPERBARIC, S.A., Burgos (ES)

(72) Inventors: Raúl Lopez Ondevilla, Burgos (ES); Rubén Garcia Reizabal, Burgos (ES); Santiago Tarrago Mingo, Burgos (ES); Andrés Felipe Hernando Saiz, Burgos (ES)

(73) Assignee: HIPERBARIC, S.A., Burgos (ES)

( * ) Notice: Subject to any disclaimer, the term of this patent is extended or adjusted under 35 U.S.C. 154(b) by 497 days.

(21) Appl. No.: 17/270,724

(22) PCT Filed: Aug. 24, 2018

(86) PCT No.: PCT/ES2018/070572
§ 371 (c)(1),
(2) Date: Feb. 23, 2021

(87) PCT Pub. No.: WO2020/039106
PCT Pub. Date: Feb. 27, 2020

(65) Prior Publication Data
US 2021/0212346 A1 Jul. 15, 2021

(51) Int. Cl.
*A23L 3/015* (2006.01)
*A23L 2/42* (2006.01)
(Continued)

(52) U.S. Cl.
CPC ............... *A23L 3/0155* (2013.01); *A23L 2/42* (2013.01); *A23L 3/001* (2013.01); *A61L 2/02* (2013.01);
(Continued)

(58) Field of Classification Search
CPC ........ A23L 3/0155; A23L 3/001; A23L 3/003; A23L 2/42; A61L 2/02; A61L 2/26;
(Continued)

(56) References Cited

U.S. PATENT DOCUMENTS

| | | | |
|---|---|---|---|
| 5,993,172 A | 11/1999 | Schuman et al. | |
| 6,305,913 B1 | 10/2001 | Hashish et al. | |
| 2010/0086420 A1* | 4/2010 | Del Pozo Polidoro . | F04F 13/00 417/474 |

FOREIGN PATENT DOCUMENTS

| | | |
|---|---|---|
| JP | H0380066 A | 4/1991 |
| WO | 03092415 A1 | 11/2003 |

OTHER PUBLICATIONS

International Search Report and Written Opinion from PCT Application No. PCT/ES2018/070572, dated May 16, 2019.

\* cited by examiner

*Primary Examiner* — Jennifer Wecker
*Assistant Examiner* — Brady C Pilsbury
(74) *Attorney, Agent, or Firm* — Workman Nydegger

(57) ABSTRACT

System for protecting and securing bags for bulk high pressure processing equipment including at least one tube provided with holes, covers for evacuating and connecting the ends of the tube or tubes, the tube or tubes being anchored to the covers, a protector for the bag adapted to lengthen the outlet path of the processed product once the depressurization of the equipment is produced, and a fitting for the protector for connecting the protector to the cover on the side from which the product in the bag comes out.

16 Claims, 4 Drawing Sheets

(51) Int. Cl.
*A23L 3/00* (2006.01)
*A61L 2/02* (2006.01)
*A61L 2/26* (2006.01)

(52) U.S. Cl.
CPC .............. *A61L 2/26* (2013.01); *A23V 2002/00* (2013.01); *A61L 2202/121* (2013.01); *A61L 2202/122* (2013.01); *A61L 2202/23* (2013.01)

(58) Field of Classification Search
CPC ......... A61L 2202/121; A61L 2202/122; A61L 2202/23; A23V 2002/00
See application file for complete search history.

SYSTEM FOR PROTECTING AND SECURING BAGS IN BULK HPP EQUIPMENT AND ASSOCIATED METHOD

The present invention belongs to the sector of apparatuses and methods for high pressure processing of substances known as "pumpable", in particular but not limited to fluids such as beverages, cosmetics, etc.

BACKGROUND OF THE INVENTION

High pressure processing (HPP) is a technology that uses pressures greater than 4,000 bar to reduce the microbial load of a product without altering the characteristics thereof.

HPP equipment known for treating liquids or other substances with high pressure are based on the processing of the product previously arranged in flexible packaging, for example bottles. The classic way of high pressure processing is performed in batches of packaged products, in other words, by means of a discreet and non-continuous process. Initially, the products inside the flexible final packaging thereof are loaded into containers (made of rigid plastic) that are inserted into a steel vessel that is subsequently filled with a pressurisation fluid, generally water, leaving unoccupied gaps between the packaging. Once the vessel is full, it is completely closed and water starts to be pumped at high pressure through one or several high pressure intensifiers until reaching 4,000-6,000 bar. Said pressure is maintained for a time that can vary from seconds to several minutes. The pressure reached and the time that this pressure is maintained are the main parameters of the process and they are defined in each case based on the product that is going to be processed (which is commonly called the "recipe"). For example, in the case of a beverage, the technology is used for the effect of inactivating microorganisms therein and the recipe is defined based on the level of microorganism inactivation that is to be reached. Finally, the pressure is released, the containers are taken out of the inside of the vessel and the processed product is removed. The product has been sanitised, meaning that the microbial load has been reduced.

In an HPP process the pressure is transmitted to the product through the pressurisation fluid, hence the pressure is transmitted equally and instantaneously to all the points of the product. Given that the product is processed while already packaged, the filling coefficient of the vessels (relationship between the product volume to be processed and the useful volume of the vessel) is low, between 40% and 60%, depending on the geometry of the packaging and the diameter of the vessel. The main advantage of processing in batches is the absence of subsequent contamination of the product, since from the beginning it is in the final packaging thereof. On the other hand, the main disadvantage is that the low filling coefficient reached limits the productivity of traditional high pressure processing equipment. Other disadvantages of batch processing are the need to use flexible packaging that supports the effects of the high pressures, it not being possible to use materials such as glass, and the need to handle them for the loading and unloading of the HPP machine.

Therefore, the need arises to search for an alternative to the current way of processing that successfully increases the filling coefficient of the vessel and avoids the restrictions of this type of packaging, ensuring that after the processing of the product no contamination is produced, this last one being the most complicated to accomplish.

Over time, different solutions have been proposed, one of these consisting of processing liquids inside a bag or flexible membrane situated inside the vessel and which occupies the largest useful space possible.

To make a distinction with HPP processing of already packaged products, the process with a bag or membrane is called bulk HPP. For the sake of simplicity, hereinafter we will call the bag or membrane simply a bag.

Examples of bulk HPP systems are the ones described in U.S. Pat. No. 5,993,172A or U.S. Pat. No. 6,305,913B1, where different systems for bulk HPP of pumpable substances are shown.

One of the challenges of bulk HPP equipment is ensuring that the pressurisation fluid (generally water) and the pumpable substance are not able to mix. To do so, two things must be ensured: that the connection of the bag is completely sealed and that it does not get broken.

In reference to FIG. 1, the sequence of operations of bulk HPP equipment consists of the following steps:

1. Filling of the bag 2 with the pumpable substance, through the valve 5 and the plug 3a. To vent the air inside the vessel 1, the unloading valves 6a and 6b are opened and the air leaves towards the outside through ducts 8a and 8b or the air could also be vented through a valve situated in any of the two plugs. The filling can also be performed through a valve 5 situated in the opposite plug as shown in FIG. 5.
2. Pressurisation of the vessel 1 by pumping water at a high pressure through the ducts 7a and 7b. The pressurised water stays inside the vessel 1 and on the outside of the bag 2.
3. Maintenance of the pressure inside the vessel 1 for a time predetermined by the operator when selecting the recipe.
4. Depressurisation. The pressure is unloaded by releasing the water from the inside of the chamber towards the outside through the unloading valves 6a and 6b and the ducts 8a and 8b.
5. Emptying of the bag, preferably aseptically and through the same filling valve 5 or another valve that could be enabled in any of the plugs 3a or 3b, but always in the plug to which the protection means 13 are connected.

The filling step can present problems for the integrity of the bag, since if the amount of litres introduced is not controlled well it is possible to break the bag with the pumping pressure itself. However, breakage can also occur in the chamber depressurisation step. During this step the pressurised water, which can be at 6,000 bar, is released by instantaneously opening the unloading valves 6a and 6b. In order for the pressure to be the same as the atmospheric pressure, it is necessary for the amount of water that leaves to be the same as the amount introduced in the pumping step. Given that liquids tend to move from areas with higher pressure to areas with lower pressure and given that both the water and the pumpable substance are at the same pressure, both fluids tend to move to the outside when valves 6a and 6b are opened, such that the pumpable substance, in the intent thereof to move towards the outside of the vessel, drags the bag along the unloading path until it breaks.

Furthermore, it is possible for the pressurisation water to not be distributed homogeneously on both sides of the vessel due to multiple reasons, such as having more pumps connected on one side than the other, or that, during unloading, the valves do not open at exactly the same time which makes more water come out on one of the sides.

The problem of this asymmetric distribution of the water in the vessel is that, when the depressurisation occurs, given that on one side there is less fluid, the bag will tend to be dragged by the unloading duct on that side. Furthermore, it is possible that small pools of water form in points of the central area of the vessel 1, the contents of which do not find an outlet path towards the unloading valves during the depressurisation step. As mentioned above, if all the pressurisation water does not leave the vessel, that which will tend to leave will be the pumpable substance, breaking the bag.

Another step where the bag can be damaged by suction is in the emptying step, since it can be dragged towards the outlet path of the valve 5. Apart from breakage, this phenomenon can give rise to said unloading path for the product to become blocked, in this way making the emptying of the bag impossible.

DESCRIPTION OF THE INVENTION

The object of the present invention is that of providing a system and a method that prevents differences in the distribution of the pressurisation fluid inside the vessel, the possible formation of pools of water far from the unloading areas and excess pressures generated during the filling and emptying steps of the vessel at high pressure of an HPP equipment from being a problem for the integrity of the bag or hindering the unloading of the product.

To do so, the system of the present invention provides a bag protection and securing system for bulk high pressure processing equipment provided with at least one tube with holes, covers for evacuating and connecting the ends of the tube or tubes, the tubes being, in the case that there are two or more, anchored to said covers in positions that are optionally symmetrical with respect to the central shaft of the covers; protection means for the bag adapted to lengthen and thus facilitate the outlet path of the processed product once the depressurisation of the equipment is produced and a fitting for the protection means from the bag to the cover on the side from which the product in the bag leaves. Advantageously, the holes of the tube or tubes are oriented towards the inner face of the vessel. The protection means preferably have a spiral, mesh, strap or cylinder shape with holes and they extend inside the bag to at least ¾ of the length thereof. The tube or tubes have a circular, oval or square cross section. The holes of the tube or tubes preferably have a diameter between 2 mm and 10 mm. The covers for evacuation and connection are optionally provided with conduits for the outlet of the pressurisation fluid and the tube or tubes are provided with a telescopic section.

The invention further comprises high pressure processing equipment comprising the system of the invention and a method for the use thereof.

DESCRIPTION OF THE FIGURES

In order to assist in a better understanding of the characteristics of the invention and to complement this description, the following figures, of illustrative and non-limiting nature, are attached.

DETAILED DESCRIPTION

Figure 1:
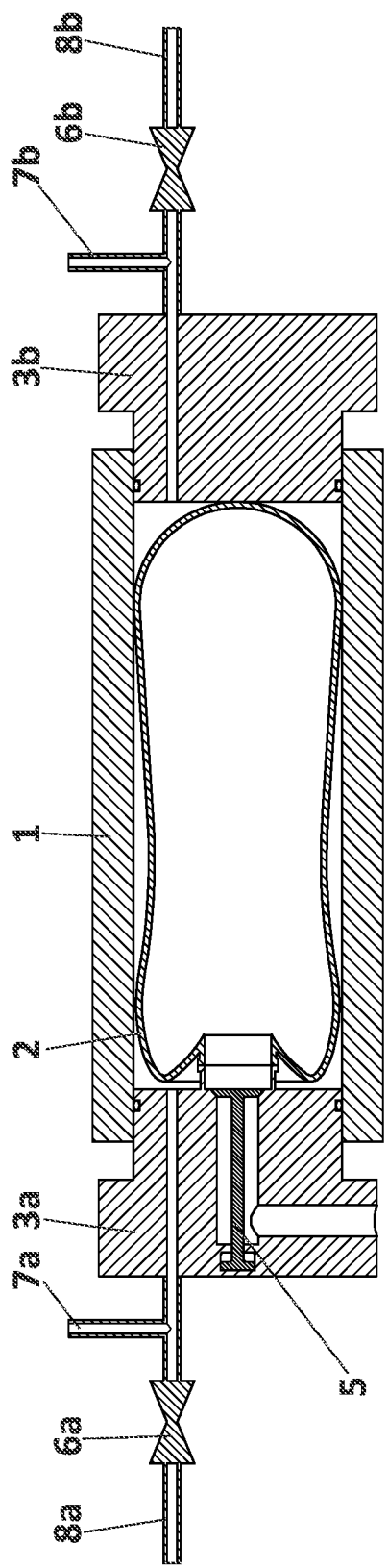
FIG. 1 shows a diagram of a possible bulk HPP system according to the state of the art.
Figure 2:
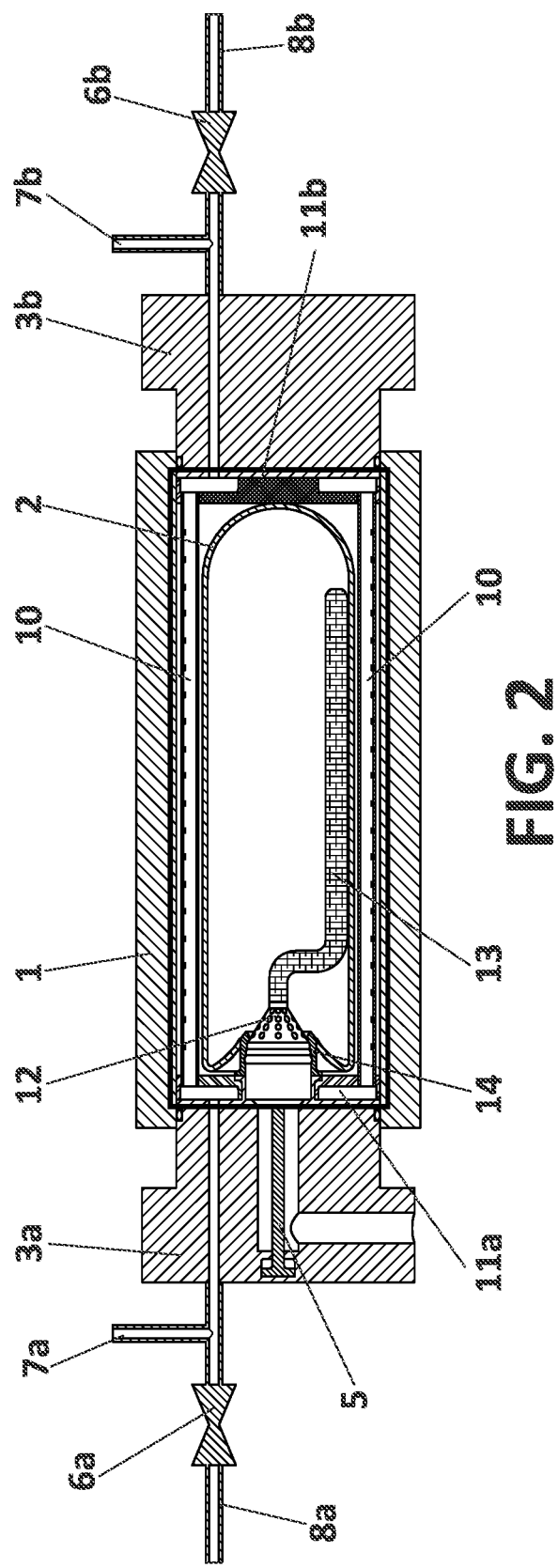
FIG. 2 is a diagram of the HPP system incorporating the invention.
Figure 3:
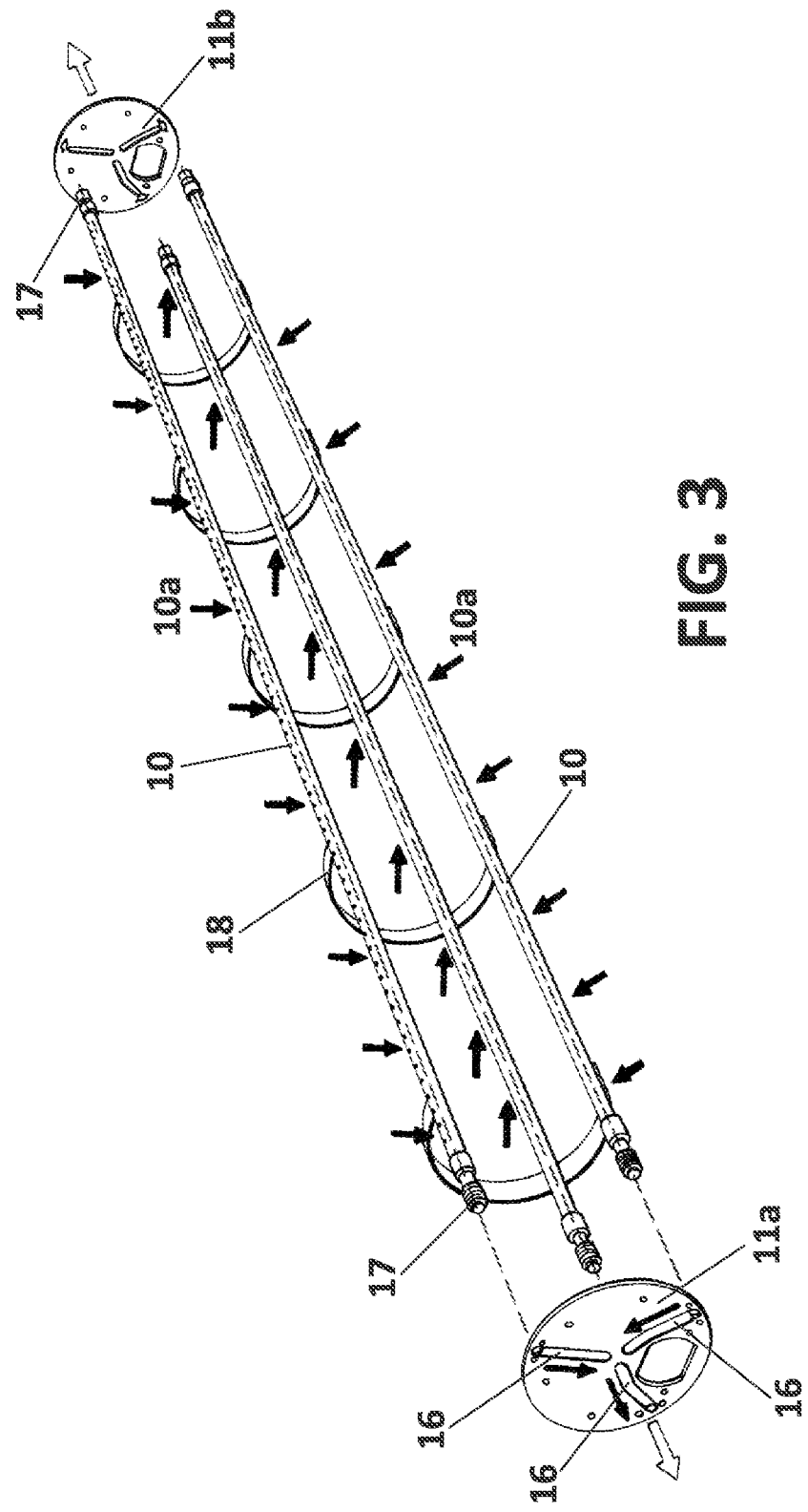
FIG. 3 shows details of the bag protection and securing system according to the invention.

In reference to FIGS. 2 and 3, the system for protecting and securing the bag is made up of perforated tubes 10 that extend along the inside of the vessel 1 (although 3 are shown in the figures, there could be from a single tube up to twenty) and covers for evacuating and connecting the ends of the tube or tubes 11a and 11b. It is further provided with means for protecting the bag 13 that aim to facilitate the outlet path of the processed product. By facilitating the outlet path of the treated product, the pressure on the bag is diminished. They are therefore any lengthened means having an increased surface along which the treated product is distributed and they have a spiral, mesh, strap or cylinder shape with holes. The protection means extend inside the bag and have at least ¾ of the length thereof. The means 13 are secured to the fitting 14 of the plug 3a through a support 12. The product can pass through the fitting 14. The means 13 are preferably manufactured from stainless steel, which gives them the sufficient rigidity to not collapse during the emptying of product due to the pressure on the outside of the bag and makes them resistant to corrosion that the different products can produce. The support 12 is provided with holes. The means 13 and the support 12 protect the integrity of the bag during the emptying of the product and prevent the bag from being sucked through the outlet circuit, since they lengthen the outlet path for the product and make the suction not focus rapidly on one point with a narrow diameter at the outlet of the bag but rather on an increased surface. In this manner, the bag, if collapsed, does so on the protection means and not on a small area.

Figure 4:
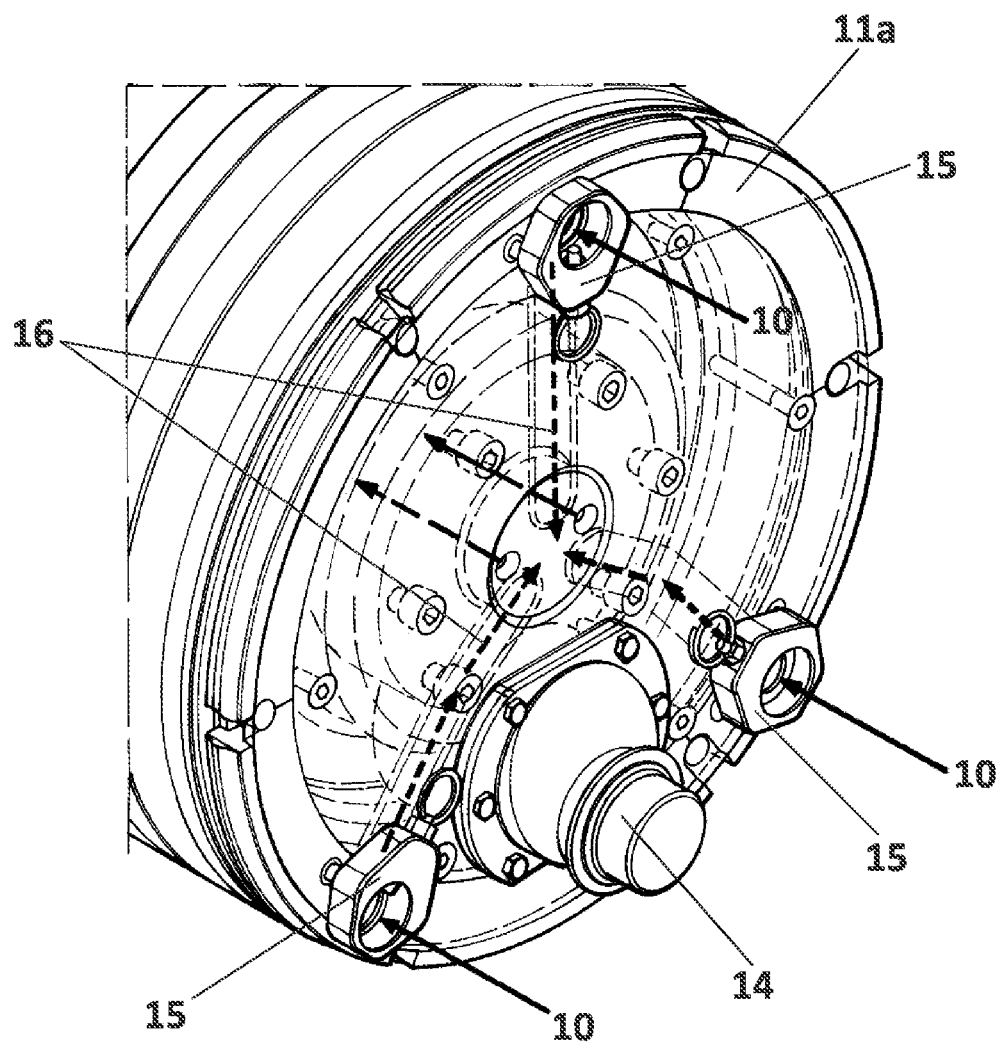
FIG. 4 shows the cover of the side through which the product is inserted according to the invention.

The covers 11a and 11b for evacuating and connecting the ends of the tube or tubes are manufactured from stainless steel in order to support on one side the stresses created during the high-pressure unloading and to be resistant to the corrosion produced by the pressurisation fluid. They guarantee continuity in the outlet path of said fluid and eliminate the risk of suction of the bag at any point. Through the covers, which are provided with channels 16, the unloading path 8a, 8b is connected to the tube or tubes 10. The connection of the tube or tubes 10 to the covers for evacuating and connecting 11a and 11b is made through mechanical means, preferably with quick connection to facilitate the operation. Each one of the tubes 10 is manually inserted into the housings of the anchoring points 15 (FIG. 4) in both covers and they are locked mechanically.

Figure 5:
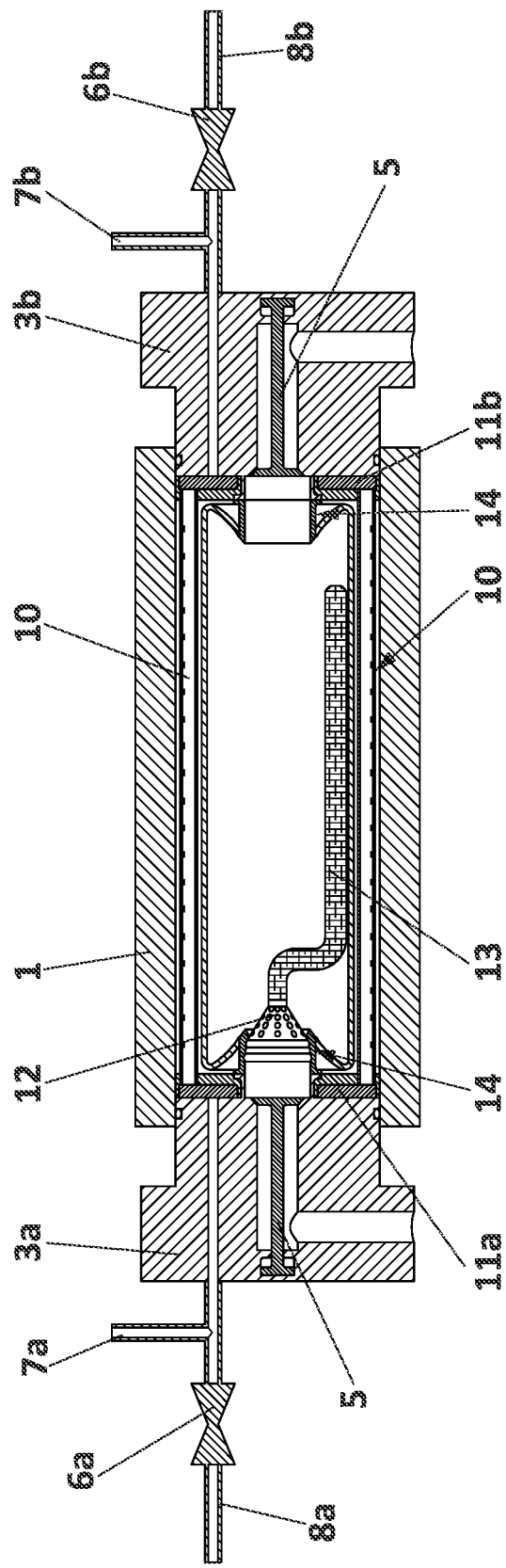
FIG. 5 shows an implementation with a filling valve on the side opposite from the emptying valve, wherein the bag is connected to 2 plugs, one for filling and the other for emptying.

The cover 11a through which the product enters is provided with a housing for the fitting 14. The opposite cover 11b is provided with the channels 16 but not with the housing for the fitting in the case in which the product enters and leaves through the same valve. Otherwise, (see FIG. 5) the cover 11b will be provided with a fitting for the product inlet.

The protection and securing system in the assembly thereof provides the following advantages:

i. Supplying a path for the suitable evacuation of the air contained in the vessel during the filling of the bag.

ii. Supplying a quick evacuation path for the pressurisation water during the unloading, thereby protecting it from the suction and consequent perforation of the bag.

iii. Acting as an anchoring point for the treatment bag during the successive cycles, preventing the movement or twisting that could be produced during the different process phases.

The perforated tube or tubes 10 have a section preferably without edges that can mark the bag and damage it when it is full. They can have a circular, square, elliptical or other shape. The number of tubes is variable, preferably three and the dimensions thereof are, preferably but not necessarily, between 20 and 40 mm in diameter. The length of this tube or tubes corresponds to the distance between plugs of the machine. In at least one of the ends of the tube a telescopic section is foreseen which enables the connection thereof to the covers when these are outside the vessel, in the bag assembly phase, since the distance between covers will be reduced in the step before the subsequent pressurisation. The tube or tubes have outlet/inlet holes 10a. The diameter thereof is preferably between 2 and 10 mm. The holes can also have a slot shape or have different diameters. They are arranged along the entire length of the tube, oriented towards the inner face of the vessel 1 such that the bag 2, located in the inner space defined by the tubes 10, in the case of there being more than one, cannot reach these holes during the high pressure unloading phase, thus preventing the possible suction of the bag 2 and the consequent breakage thereof.

Possible materials for the tube or tubes are 316 stainless steel or plastic, in order to minimise the risks of metal-metal contact with the vessel and the consequent damage to it. On both ends of the tube or tubes 10, sliding and fastening bushings 17 are arranged in order to enable and limit the movement of the telescopic tubes and prevent contact of the tube or tubes 10 with the vessel 1. Furthermore, the bushings have the function of an anchoring point for the bag in order to keep it in the correct position throughout all the cycles in which it will be used, as will be seen further on. The bushings can be manufactured from plastic material, preferably high-density PE. Furthermore, tube spacers 18 made of preferably plastic material are arranged, the main function of which is to keep the tubes 10 joined and conveniently orient them with the holes towards the vessel. They also prevent the contact of said tubes with the vessel 1 and further act as support points for the treatment bag during the insertion and extraction phases of the processing vessel. In the case of there only being one tube, the spacers 18 would continue to orient it with the holes towards the vessel and would also prevent the contact of the tube with the vessel, as well as continuing to act as support points for the treatment bag. The joint of the spacers 18 and the tube or tubes 10 is preferably made with non-metal fittings.

The process of bulk HPP treatment by means of equipment incorporating the system of the invention is as follows:

1. Placement of the bag:

A table for preparing and loading the bag is arranged at the inlet of the vessel. The tube or tubes 10 and spacers 18 act in this step as support for the fastening of the bag and the subsequent insertion thereof into the vessel 1.

The bag is joined to the bushings 17 by means of elastic bands in order to maintain the fixed position thereof in successive cycles that will be performed with it and prevent possible movements or twisting that can be produced due to the effects during the phases of the process such as the high pressure unloading.

Afterwards, the protection means 13 and the support 12 are inserted into the bag.

2. Insertion of the assembly into the vessel:

With the vessel 1 in a position aligned with a table for preparing the bag, the assembly of tube or tubes 10 and spacers 18 with the bag 2 incorporated is pushed until it is completely inserted into the vessel 1.

3. Moving of vessel to the working position:

The vessel is aligned with the yoke, in the processing position.

4. Connection of tube or tubes 10 and spacers 18 to the evacuation and connection covers 11:

The bag 2 is connected to the fitting of the product plug 14.

The perforated tube or tubes 10 connect to both evacuation and connection covers 11a and 11b. The connection is made manually. The anchoring is performed by means of a quick fastening system.

5. Closing of vessel:

The plugs and wedges of the machine are closed. The machine is ready for the beginning of the cycle.

6. Prefilling of vessel:

A small amount of water is introduced into the vessel (on the outside of the bag) which will act to fill in the uncovered spaces with it. Thus, the bag is protected during the product filling phase, since the water exerts a counter pressure. This step also has the aim of reducing the amount of water to be introduced by the high pressure pumps and therefore accelerating the cycle.

7. Filling of bag:

Filling of the bag 2 with the product to be treated. The tube or tubes 10 of the protection and securing system act in this phase to help to properly evacuate the air from the inside of the vessel through the holes 10a. The product enters through the valve 5, which can be in any of the two plugs.

8. Pressurisation, maintenance and unloading:

The high pressure cycle is started. The pressurisation water enters through the ducts 7a and 7b through the covers 11a and 11b and is distributed through the perforated tube or tubes 10. The pressurisation water stays in the surroundings of the tube or tubes. After maintaining the pressure during the time defined by the recipe, the pressure of the vessel is released through the ducts 8a and 8b. The water finds the path thereof through the tube or tubes 10 and covers 11a and 11b towards the atmosphere. The function of the tube or tubes is to prevent the suction of the bag during this phase.

9. Emptying of the bag:

In order to empty the bag of the already treated product, a pressurised fluid is introduced into the vessel and on the outside of the bag.

10. Consecutive cycles:

The processing bag has to support a series of consecutive cycles. Once the production of a certain type of product has ended, the estimated limit on the number of cycles has been reached or a breakage of the bag has been detected, the bag is then changed, repeating the previous process in reverse from point 5.

In view of this description and figures, the person skilled in the art will understand that the invention has been described according to preferred embodiments thereof, but that multiple variations can be made to said preferred embodiments without departing from the object of the invention as has been claimed.

The invention claimed is:

1. A system for protecting and securing bags for bulk high pressure processing equipment, the system comprising:
    one or more tubes provided with holes;
    covers for evacuating pressurization fluid and connecting ends of the one or more tubes, the one or more tubes being anchored to said covers;
    a bag protector that protects a bag that lengthens an outlet path of a processed product once depressurization of the pressure processing equipment is produced, said bag protector having a cylinder shape with holes or a spiral, mesh, or strap; and a fitting for the bag protector for connecting the bag protector to the cover on a side of the system from which the processed product in the bag comes out.

2. The system for protecting and securing bags according to claim 1, wherein the holes of the tube or tubes are oriented towards an inner face of a processing vessel in which the system for protecting and securing bags extends.

3. The system for protecting and securing bags according to claim 1, wherein, the bag protector extends inside the bag along at least ¾ of the length thereof.

4. The system for protecting and securing bags according to claim 1, wherein the one or more tubes have a circular, oval or square cross section.

5. The system for protecting and securing bags according to claim 1, wherein the holes of the one or more tubes have a diameter between 2 mm and 10 mm.

6. The system for protecting and securing bags according to claim 1, wherein the covers for evacuating pressurization fluid are provided with conduits for an outlet of the pressurization fluid.

7. The system for protecting and securing bags according to claim 1, wherein the one or more tubes are provided with a telescopic section.

8. A unit of high-pressure processing equipment comprising:
a processing vessel;
a bag; and
a system for protecting and securing the bag, the system including
one or more tubes provided with holes;
covers for evacuating pressurization fluid and connecting ends of the one or more tubes, the one or more tubes being anchored to said covers;
a bag protector that protects the bag that lengthens an outlet path of a processed product once depressurization of the pressure processing equipment is produced, said bag protector having a cylinder shape with holes or a spiral, mesh, or strap; and
a fitting for the bag protector that connects the bag protector to the cover on a side of the system from which the processed product in the bag comes out.

9. A method of high-pressure treatment by pressure processing equipment, the method comprising:

providing a unit of high-pressure processing equipment that includes
a processing vessel,
a bag, and
a system for protecting and securing the bag, the system for protecting and securing the bag including
one or more tubes provided with holes,
covers for evacuating pressurization fluid and connecting ends of the one or more tubes, the one or more tubes being anchored to said covers,
a bag protector that protects the bag that lengthens an outlet path of a processed product once depressurization of the pressure processing equipment is produced, said bag protector having a cylinder shape with holes or a spiral, mesh, or strap, and
a fitting for the bag protector that connects the bag protector to the cover on a side of the system from which the processed product in the bag comes out; and
introducing an amount of pressurization fluid into the vessel that is less than the amount of fluid needed to maintain a pressure of a recipe.

10. The method according to claim 9, further comprising emptying the bag, after application of the recipe, using a pressurized fluid outside of the bag.

11. The unit of high-pressure processing equipment according to claim 8, wherein the holes of the tube or tubes are oriented towards an inner face of the processing vessel.

12. The unit of high-pressure processing equipment according to claim 8, wherein, the bag protector extends inside the bag along at least ¾ of the length thereof.

13. The unit of high-pressure processing equipment according to claim 8, wherein the one or more tubes have a circular, oval or square cross section.

14. The unit of high-pressure processing equipment according to claim 8, wherein the holes of the one or more tubes have a diameter between 2 mm and 10 mm.

15. The unit of high-pressure processing equipment according to claim 8, wherein the covers for evacuating pressurization fluid are provided with conduits for an outlet of the pressurization fluid.

16. The unit of high-pressure processing equipment according to claim 8, wherein the one or more tubes are provided with a telescopic section.

* * * * *